(12) United States Patent
Docimo et al.

(10) Patent No.: US 12,710,580 B2
(45) Date of Patent: Aug. 18, 2026

(54) FIBEROPTIC CABLE SAFETY DEVICES

(71) Applicants: University of Pittsburgh—Of the Commonwealth System of Higher Education, Pittsburgh, PA (US); UPMC, Pittsburgh, PA (US)

(72) Inventors: Steven Gerard Docimo, Philadelphia, PA (US); William W. Clark, Wexford, PA (US); Alexandra Marie Delazio, Pittsburgh, PA (US); John A. Holmes, Wexford, PA (US); Benjamin T. Ristau, Philadelphia, PA (US)

(73) Assignees: University of Pittsburgh—Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 544 days.

(21) Appl. No.: 18/065,485

(22) Filed: Dec. 13, 2022

(65) Prior Publication Data

US 2023/0110584 A1 Apr. 13, 2023

Related U.S. Application Data

(63) Continuation of application No. 16/077,229, filed as application No. PCT/US2017/017171 on Feb. 9, 2017, now Pat. No. 11,534,051.

(Continued)

(51) Int. Cl.
*A61B 90/30* (2016.01)
*F21V 8/00* (2006.01)

(Continued)

(52) U.S. Cl.
CPC ............ *G02B 6/0036* (2013.01); *A61B 90/30* (2016.02); *G02B 6/255* (2013.01); *G02B 6/36* (2013.01);

(Continued)

(58) Field of Classification Search
CPC .......... F16D 3/845; F16D 3/848; F16D 3/843; F16D 3/84; A61B 90/30; A61B 1/3132;

(Continued)

(56) References Cited

U.S. PATENT DOCUMENTS 1,922,431 A * 8/1933 Geyer .................... F16D 3/845 74/18.1
3,643,207 A 2/1972 Cairns (Continued)

FOREIGN PATENT DOCUMENTS

CN 203417184 2/2014
JP H07-191266 7/1995

(Continued)

OTHER PUBLICATIONS

Assael et al., "Thermal Conductivity of Polymethyl Methacrylate (PMMA) and Borosilicate Crown Glass BK7," *Int'l Journal of Thermophysics*, vol. 26, No. 5, pp. 1595-1605 (Sep. 2005).

(Continued)

*Primary Examiner* — Ismael Negron
(74) *Attorney, Agent, or Firm* — Klarquist Sparkman, LLP

(57) ABSTRACT

Safety devices that are positioned on the end of a fiberoptic cable and assemblies including a safety device and a fiber optic cable. The safety devices can include an annular adaptor for receiving a connector of a fiber optic cable and an end cover coupled to the annular adaptor that is moveable between a relaxed state and an elastically deformed state. In the elastically deformed state, a free edge of the end cover is deformed radially outwardly and is axially displaced along a longitudinal axis of the safety device such that the connector of the fiberoptic cable can be coupled to an engagement portion of an optical medical instrument. In the relaxed state, a plane of a distal face of the end cover is (Continued)

perpendicular or substantially perpendicular to a longitudinal axis of the safety device to cover a distal end of the fiber optic cable.

20 Claims, 15 Drawing Sheets

Related U.S. Application Data

(60) Provisional application No. 62/300,431, filed on Feb. 26, 2016.

(51) Int. Cl.
*G02B 6/255* (2006.01)
*G02B 6/36* (2006.01)
*G02B 6/42* (2006.01)

(52) U.S. Cl.
CPC ............. *G02B 6/42* (2013.01); *G02B 6/4203* (2013.01); *G02B 6/424* (2013.01)

(58) Field of Classification Search
CPC ..... A61B 1/0669; A61B 1/00126; A61B 1/06; G02B 6/0036; G02B 6/255; G02B 6/36; G02B 6/424; G02B 6/4296; B65D 47/44; B65D 47/4296; B65D 47/36; B65D 47/06; A47G 19/2222
USPC ...................................... 49/34, 42, 306, 310
See application file for complete search history.

(56) References Cited

U.S. PATENT DOCUMENTS 3,747,369 A * 7/1973 Morin ....................... F16D 3/24 464/157
3,798,927 A * 3/1974 Girguis ................... F16D 3/845 464/146
3,849,864 A * 11/1974 Plummer ................ B29C 53/30 29/454
4,116,020 A * 9/1978 Aucktor .................. F16D 3/224 464/145
4,411,491 A * 10/1983 Larkin ................. G02B 6/3849 385/59
4,413,880 A 11/1983 Forrest et al.
4,578,034 A 3/1986 Shibata et al.
4,592,353 A 6/1986 Daikuzono
4,606,603 A 8/1986 Cairns
4,649,616 A 3/1987 Bricker et al.
4,673,242 A 6/1987 Logan et al.
4,785,805 A 11/1988 Joffe et al.
4,895,145 A 1/1990 Joffe et al.
4,927,203 A * 5/1990 Mayer ..................... E05B 81/25 292/201
4,932,948 A * 6/1990 Kernes .................... A61F 5/453 128/885
4,957,469 A * 9/1990 Zollinger ................ F16D 3/845 464/175
4,989,884 A * 2/1991 Goodman ................. F16F 9/38 277/928
5,009,122 A * 4/1991 Chaczyk ................... F16C 1/12 74/502
5,147,065 A * 9/1992 Rush ...................... B65D 47/36 215/229
5,251,916 A * 10/1993 Martin .................... F16D 3/845 277/944
5,308,091 A * 5/1994 Mihalcin .................. F16J 3/041 277/636
5,356,593 A 10/1994 Heiberger et al.
5,415,157 A * 5/1995 Welcome ............... A61B 46/10 206/592
5,452,391 A * 9/1995 Chou ................... G02B 6/4296 385/53
5,549,594 A 8/1996 Brunken
5,556,310 A * 9/1996 Gandarillas ........... F02B 61/045 440/53
5,570,445 A 10/1996 Chou et al.
5,695,202 A * 12/1997 Cartwright .............. F16D 3/845 277/636
5,709,668 A 1/1998 Wacks
6,134,789 A * 10/2000 Strickland .............. A01D 34/84 30/DIG. 7
6,280,102 B1 8/2001 Go
6,299,014 B1 * 10/2001 Nava ...................... B65D 51/28 206/217
6,315,461 B1 * 11/2001 Cairns .................. G02B 6/3816 385/139
6,464,405 B2 * 10/2002 Cairns .................. G02B 6/3816 385/139
6,496,625 B1 12/2002 Falkowich et al.
6,612,750 B1 9/2003 Bull et al.
7,035,689 B1 4/2006 Hawkins et al.
7,056,151 B2 6/2006 Cawood et al.
7,208,855 B1 4/2007 Floyd
7,681,750 B2 * 3/2010 Jackel ................ B65D 47/2037 215/310
7,695,373 B1 * 4/2010 Billett ..................... F16D 3/845 464/175
7,935,091 B2 5/2011 Bousquet
7,991,260 B2 8/2011 Doody et al.
10,018,229 B2 * 7/2018 Hector .................... F16D 3/845
11,390,431 B2 * 7/2022 Bradley ............. B65D 51/1644
11,534,051 B2 * 12/2022 Docimo ............... G02B 6/0036
2002/0065450 A1 * 5/2002 Ogawa .................. A61B 1/126 600/157
2004/0064019 A1 * 4/2004 Chang .................... A61B 1/045 600/118
2004/0171283 A1 9/2004 Ngo
2005/0036755 A1 2/2005 Horne
2006/0037977 A1 * 2/2006 Eimer ................ B65D 47/2031 222/494
2006/0204200 A1 9/2006 Lampert et al.
2006/0255093 A1 11/2006 Wimroither et al.
2006/0264842 A1 * 11/2006 Fangrow, Jr. ......... A61M 39/02 604/247
2007/0292098 A1 12/2007 Kokkinos
2008/0249478 A1 10/2008 Ishikura et al.
2008/0317428 A1 12/2008 Nakagawa
2010/0044965 A1 * 2/2010 Lou ......................... F16D 3/845 277/315
2010/0310226 A1 12/2010 Wakileh et al.
2011/0034774 A1 2/2011 Doody et al.
2012/0029360 A1 2/2012 Hendriks et al.
2013/0131453 A1 5/2013 Imai
2013/0279920 A1 10/2013 Herzog
2014/0163470 A1 6/2014 Baid
2015/0277063 A1 10/2015 Hikosaka
2015/0297063 A1 10/2015 Wolcott et al.
2016/0023822 A1 * 1/2016 Schramm ............... B65D 51/32 215/250
2016/0128755 A1 5/2016 Ho et al.
2016/0235229 A1 * 8/2016 Löhn ...................... B65D 47/06
2016/0259131 A1 9/2016 Erdman et al.
2016/0324402 A1 11/2016 Yajima
2019/0208998 A1 7/2019 Powers et al.
2019/0357761 A1 * 11/2019 Hessler .................... A61B 1/24
2024/0011529 A1 * 1/2024 Ruiz ....................... F16D 3/845

FOREIGN PATENT DOCUMENTS

JP 4406130 1/2010
WO WO 2017/146910 8/2017

OTHER PUBLICATIONS

International Search Report and Written Opinion for related International Application No. PCT/US2017/017171, mailed Apr. 27, 2017, 11 pages.
Mu et al., "Thermal Conductivity of Silicone Rubber Filled with ZnO," *Polymer Composites*, pp. 125-130 (2007).

(56) References Cited

OTHER PUBLICATIONS

Roy et al., "Reducing fire and burn risk in the operating room—testing of a novel device," *Surgical Endoscopy,* vol. 35, pp. 6969-6976 (2021).

* cited by examiner

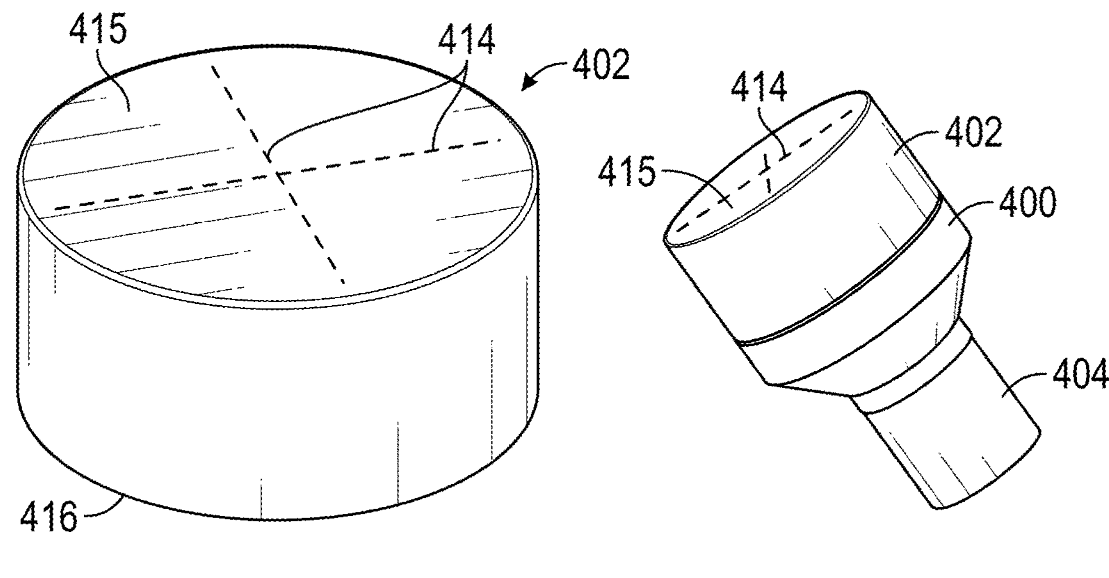
FIG. 16C
FIG. 16D
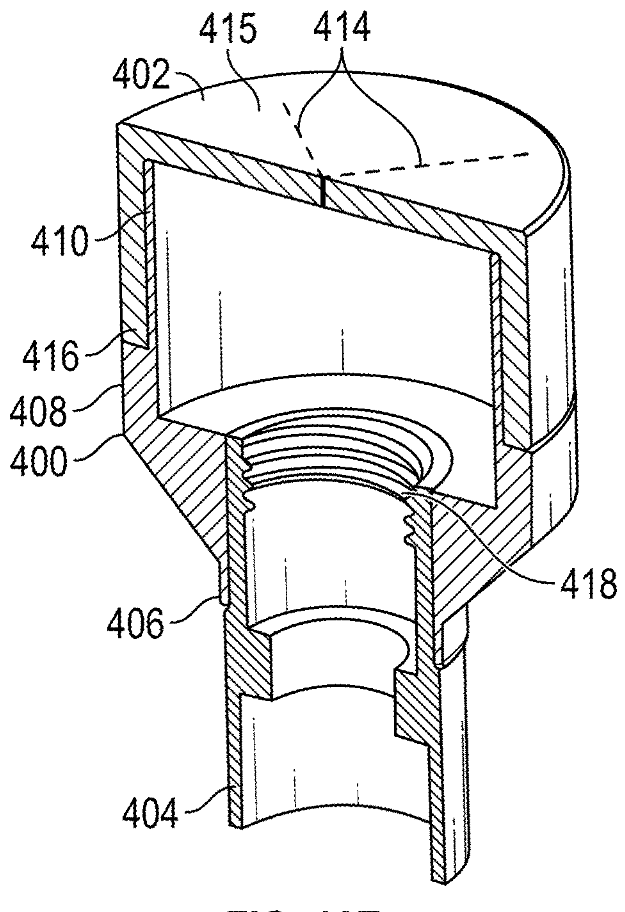
FIG. 16E

FIBEROPTIC CABLE SAFETY DEVICES

CROSS-REFERENCE TO RELATED APPLICATIONS

This application is a continuation of U.S. patent application Ser. No. 16/077,229, filed Aug. 10, 2018 and issuing as U.S. Pat. No. 11,534,051, which is the U.S. National Stage of International Application No. PCT/US2017/017171, filed Feb. 9, 2017, which claims the benefit of U.S. Provisional Application No. 62/300,431, filed Feb. 26, 2016, each of the foregoing applications incorporated by reference herein in its entirety.

FIELD

This application is related to safety devices for fiberoptic cables such as those used in medical and surgical procedures, such as laparoscopic surgery.

BACKGROUND

Minimally invasive surgical techniques have increased in popularity and use over the past several decades with current estimates of 2-3 million cases performed annually in the United States. Laparoscopic and other fiberoptic-dependent procedures use a light source that attaches to an optical instrument via a fiberoptic cable. The fiberoptic cable has two ends. The proximal end of the fiberoptic cable connects to a light source, while the distal end attaches to a lens of the laparoscopic instrument, for example. This distal end of this fiberoptic cable becomes very hot (e.g., in excess of 260° C.) during use in the operating room and poses a burn risk if it is detached from the lens prior to turning off the light source. In fact, burns to drapes, operating room fires, and burns to patients are well reported in the literature.

During normal use, it is the responsibility of the operator to request the light source be powered down or placed on "stand-by" so that the distal end of the light cord no longer poses a fire hazard. This is fraught with human error (e.g., the operator has to remember to request the light source be turned off each time the light cord is disconnected from the lens).

SUMMARY

This disclosure presents safety adaptors that are positioned on the end of a fiberoptic cable to prevent patients and other objects from the risk of burn from light emitted from the end of the cable. The disclosed safety adaptors can be added to the ends of existing cables and/or can be included at the end of cables during manufacture. In some embodiment, the safety adaptor replaces an existing connector at the end of a cable, and in some embodiments the safety adaptor is added in addition to a connector at the end of the cable. In some embodiments, a slit cover is included over the end of the adaptor.

Some disclosed adaptors can be configured to be permanently fixed to a fiberoptic cable, to not require a surgeon or other operator to carry out any steps for it to be used effectively (e.g., the surgeon does not need to change his/her typical routine from what is done with a cable that does not include the adaptor), and to effectively reduce the risk of burn from the exposed fiberoptic cable when it is detached from an instrument. This disclosed technology is different than just a removable and replaceable safety cap that is placed over the end of a fiberoptic cable after the instrument is detached, then removed when reattaching an instrument. For example, disclosed safety adaptors do not require operator intervention in order to protect the distal, "hot" end of the light cord. In the current clinical practice, the operator must remember to ask for the light source to be deactivated upon removing the light cord from the lens. A removable and replaceable safety cap still requires the operator to think to apply it. Thus, it does not remove the root cause of the fire hazard proposed by the unguarded distal end of an activated light cord (i.e. the human operator).

Disclosed safety adaptors are different in that they incorporate a fixed annular sheath that extends distally from the distal end of the fiberoptic cable at all times, including when the instrument is attached and after the instrument is detached and the light is still on. The action on the part of the operator can be the same as with a conventional fiberoptic cable with a conventional connector and no safety adaptor.

In addition, the disclosed safety adaptors both insulate the distal end of the fiberoptic cable and physically create linear distance between the distal end of the light outlet and any objects that the end of the cable might touch (skin, fabric, etc.).

Some embodiments of the disclosed safety adaptors also include a permanent or semi-permanent end cover mounted over the distal end of the adaptor. The end cover can alternatively be integral with the adaptor. The cover can include a slit opening through which the instrument is passed for connection to the cable. In contrast, typical removable safety caps are solid and temporary, and must be removed in order to attach the instrument and then replaced after removing the instrument to protect the cable. Disclosed adaptors with slit end covers are more time efficient and foolproof, thus potentially reducing procedure time by not requiring additional steps for use and reducing risk of burns or fires.

In some embodiments, the sheath portion of the adaptor is coupled to the base portion of the adaptor via a spring biasing mechanisms that allows the sheath portion to automatically recoil to a maximally extended position when an optical instrument is disconnected.

In some embodiments, the safety device comprises a semi-ridge skeleton adaptor cover with a more flexible overmold that includes the slit end cover. The skeleton can include proximally extending fingers that are radially flexible and covered with the flexible overmold to form a radially expandable proximal opening. This allows the safety device to be couplable to connectors having a range of different diameters. The overmold can be at least partially transparent and/or can include windows to allow some of the light to escape from within the device.

The foregoing and other objects, features, and advantages of the disclosed technology will become more apparent from the following detailed description, which proceeds with reference to the accompanying figures.

BRIEF DESCRIPTION OF THE DRAWINGS

FIG. 16C shows the slit cover of FIG. 16B.

FIG. 16D shows the adaptor and slit cover of FIG. 16B mounted on a conventional connector of a fiberoptic cable.

FIG. 16E is a cross-sectional view of the adaptor, cover, and connector shown in FIG. 16D.

DETAILED DESCRIPTION

Disclosed herein are several embodiments of safety adaptors that are mounted on the end of a fiberoptic cable to prevent patients and other objects from the risk of burn or light damage from light emitted from the end of the cable. The disclosed safety adaptors can be added to the ends of existing cables, can replace a connector at the end of an existing cable, and/or can be included at the end of cables during original manufacture. In some embodiments, the safety adaptor replaces an existing connector at the end of a cable, and in some embodiments the safety adaptor is added in addition to an existing connector at the end of the cable. In some embodiments, a slit cover is included over the distal end of the adaptor. Disclosed adaptors are adapted to be permanently or semi-permanently attached to the end of a fiberoptic cable and function passively without an operator needing to take any additional actions or actions different than actions typically taken when using a conventional fiberoptic cable with a conventional connector at its end.

Some disclosed adaptors are configured to be permanently fixed to a fiberoptic cable, to not require a surgeon or other operator to carry out any extra steps for it to be used effectively (e.g., the surgeon does not need to change his/her typical routine from what is done with a cable that does not include the adaptor), and to effectively reduce the risk of burn from the exposed active fiberoptic cable when it is detached from an instrument.

The potential applications for this technology are broad. In addition to the laparoscopic applications, fiberoptic light cords with the disclosed technology can be used in many endoscopic procedures including but not limited to bronchoscopy, cystoscopy, and ureteroscopy. The technology can be used to prevent thermal accidents in any industry requiring the use of detachable fiberoptic light cables. In many settings, there is a risk of burn injury to both patients and providers, as well as damage to surgical drapes and other objects. In short, surgical burns from unprotected fiberoptic light cords should be a "never" event. The Food and Drug Administration (FDA) Manufacture and User Facility Device Experience (MAUDE) database houses reported device-associated adverse events. A query over the past 10 years reveals 31 fires or burns directly attributable to fiberoptic cables. This is almost certainly an underestimation as such adverse events are likely underreported. With greater than two million laparoscopic procedures performed annually in the United States alone added to a multitude of endoscopic procedures, the proposed market for the disclosed technology is large. Moreover, there is no difference in burn risk posed by unprotected fiberoptic light cords in domestic versus international settings.

Exemplary Embodiments and Testing Results

Figure 1A:
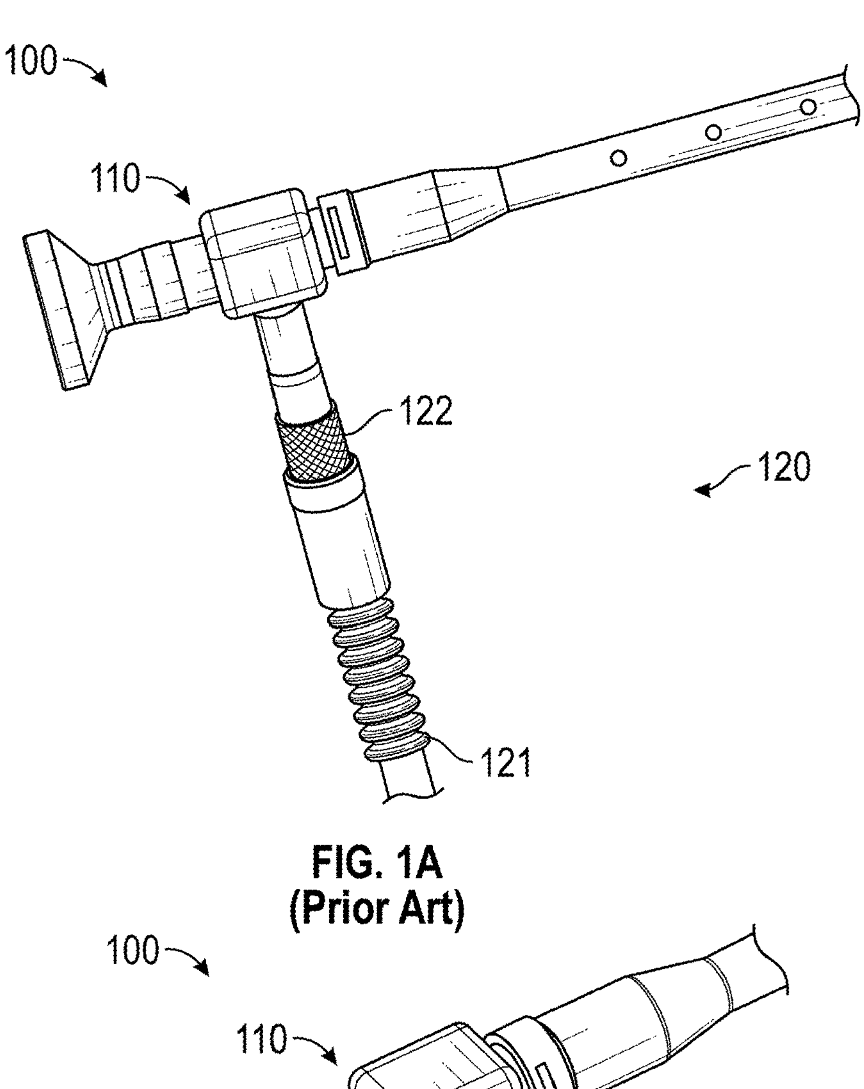
FIG. 1A shows a conventional laparoscopic instrument and fiberoptic cable when the cable is connected to the instrument.
Figure 1B:
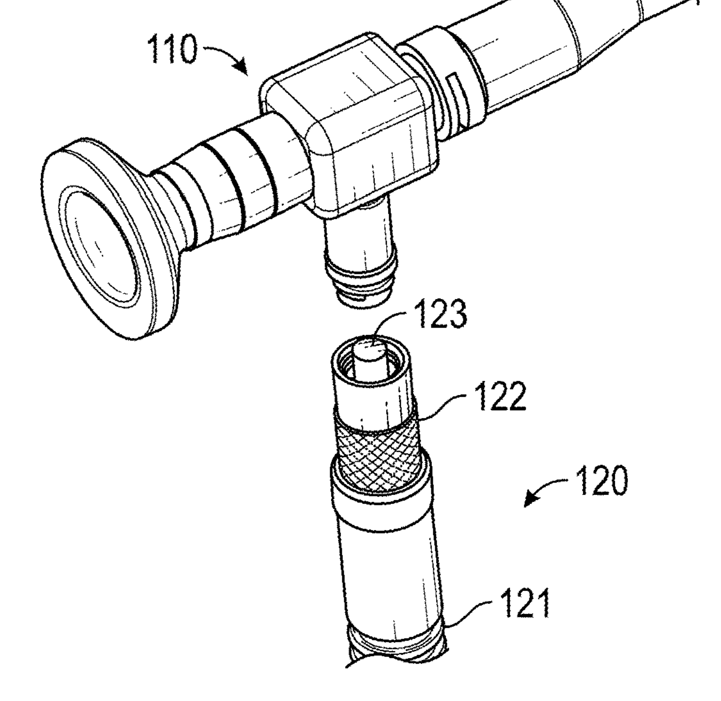
FIG. 1B shows the conventional instrument and fiberoptic cable of FIG. 1 when the cable is disconnected from the instrument showing threads on the instrument and the connector, which is one way of securing the cable to the instrument.

Disclosed safety adaptors provide an annular sheath that extends beyond the exposed light-emitting tip of the fiberoptic cable to prevent patients and surrounding materials (e.g. surgical drapes) from coming into contact with the exposed tip and to provide physical spacing between the light-emitting tip and any objects. FIGS. 1A and 1B show a conventional laparoscope assembly 100 that includes a laparoscope instrument (or other optical instrument) 110 and a fiberoptic cable assembly 120 comprising a fiberoptic cable 121, and a connector 122 (which is also referred to herein as an "internally threaded connector"). A variety of methods are employed to connect the instrument 110 to the cable assembly 120 thereby allowing light to pass from the cable to the instrument. FIGS. 1A and 1B illustrate an internally threaded connector 122, although the technology disclosed herein also can be used with other types of connectors.

Figure 2:
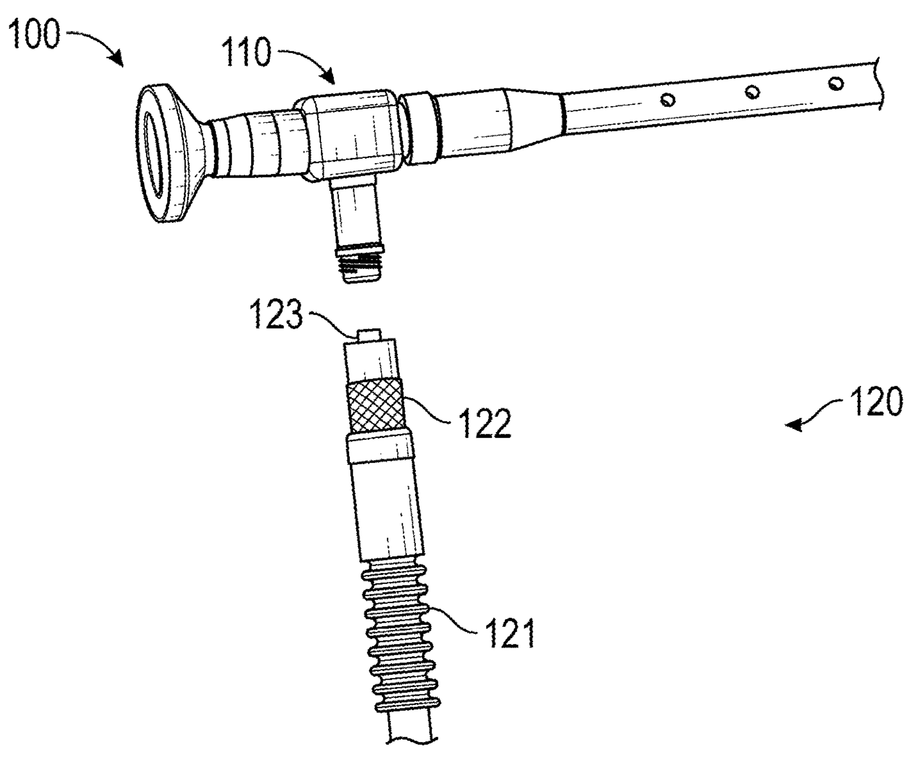
FIG. 2 shows how the hot tip of the fiberoptic cable is exposed when the cable is disconnected from the instrument.

When the optical instrument is removed, as shown in FIG. 1B and FIG. 2, the distal, light-emitting tip 123 of the optical fiber can be exposed beyond the end of the connector 122. This tip 123 becomes very hot during use, and when exposed creates a burn hazard in the operating room, especially right after the instrument 110 is disconnected. In other cable embodiments, the tip of the optical fibers may be even with or below the upper end of the connector, although the disclosed technology can still be beneficially used with such cables as well.

Figure 3:
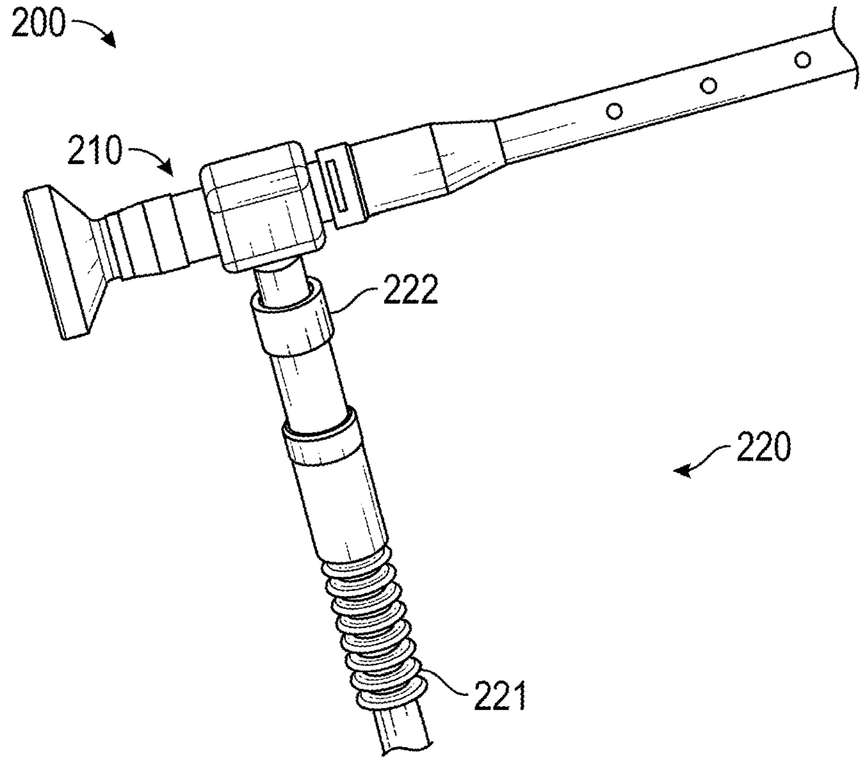
FIG. 3 shows a conventional laparoscopic instrument connected to a fiberoptic cable having an exemplary safety connector positioned at the end of the cable.
Figure 4:
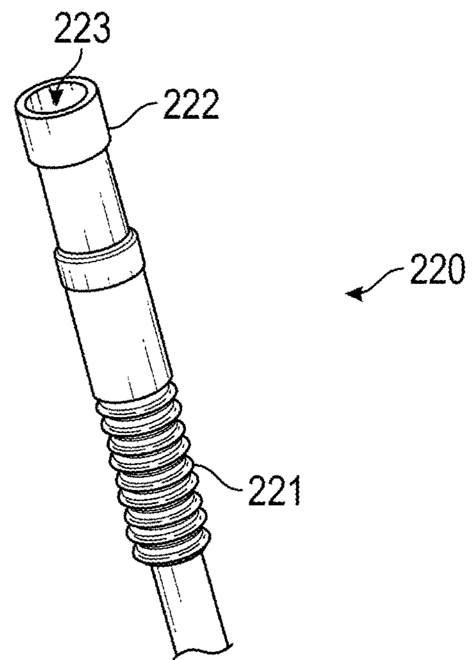
FIG. 4 shows the fiberoptic cable of FIG. 3 with the exemplary safety connector positioned at the end of the cable in place of a conventional connector.
Figure 5:
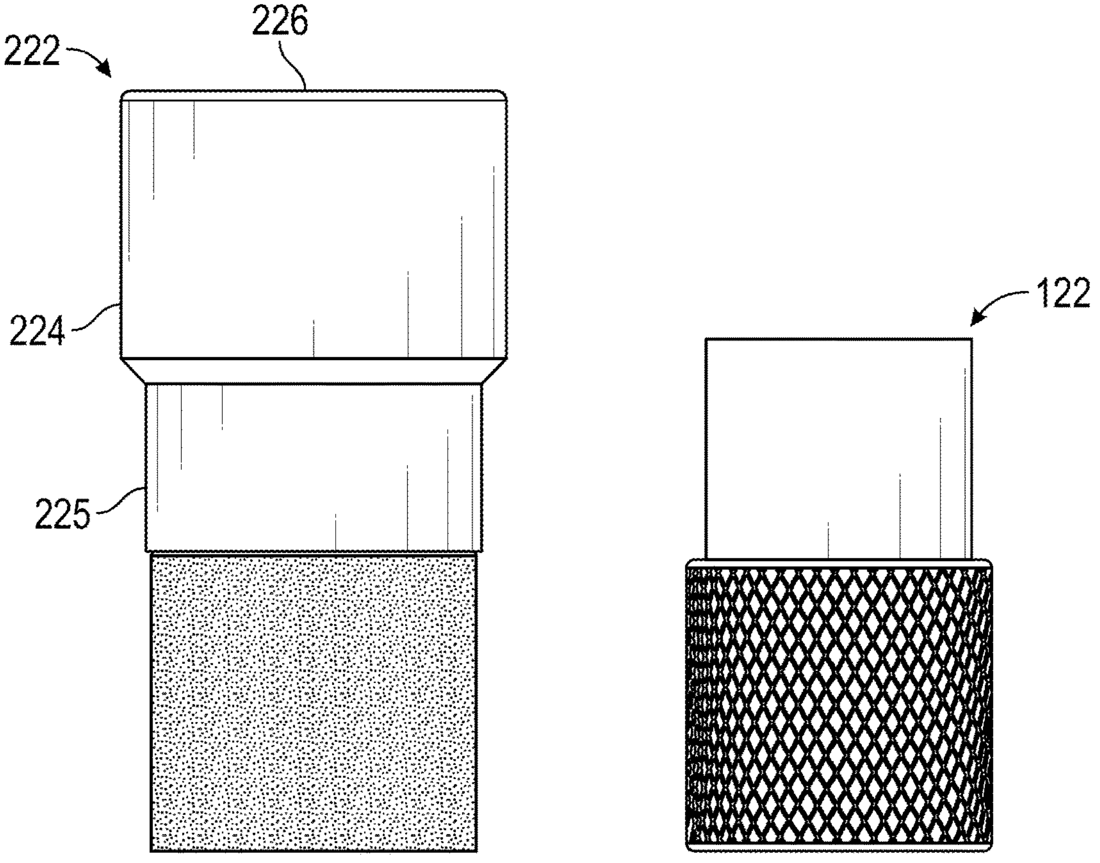
FIG. 5 shows a comparison of the conventional connector of FIGS. 1B and 2 and the safety connector of FIGS. 3 and 4.

FIG. 3 shows an exemplary laparoscope assembly 200 comprising a laparoscope instrument 210 and a fiberoptic cable assembly 220 that includes a fiberoptic cable 221 and safety connector 222 that includes a safety sheath that extends around and distally beyond the tip of the optical fiber. When the instrument 210 is removed, as shown in FIG. 4, the tip 223 of the optical fiber is not exposed, but is shrouded by the safety connector 222, reducing risk of burn. As shown in FIG. 5, the safety connector 222 includes a base section 225 that is attached to the cable and a distal sheath 224 (which is also referred to herein as an "elongated upper sheath") that extends beyond the distal tip of the optical fiber and terminates in a distal opening 226. The sheath 224 can have a wider outer diameter than the base 225.

FIG. 5 shows the safety connector 222 and the conventional connector 122 side-by-side. Both connectors are designed to be fixed to a fiberoptic cable such that the connector cannot be removed along the longitudinal axis of the cable, while the connector can optionally be free to rotate about the longitudinal axis of the cable to threadedly engage with a male connector of the optical instrument being connected. The longitudinal constraint can be enforced by a snap ring inside the connector (not shown) for example, but can alternatively be enforced by other conventional mechanical connections that provide the same degrees of restriction and freedom of motion of the connector (e.g., a lip on the cable over which the connector is forced during assembly to prevent it from being removed longitudinally but allowing rotational motion).

Figures 6, 7:
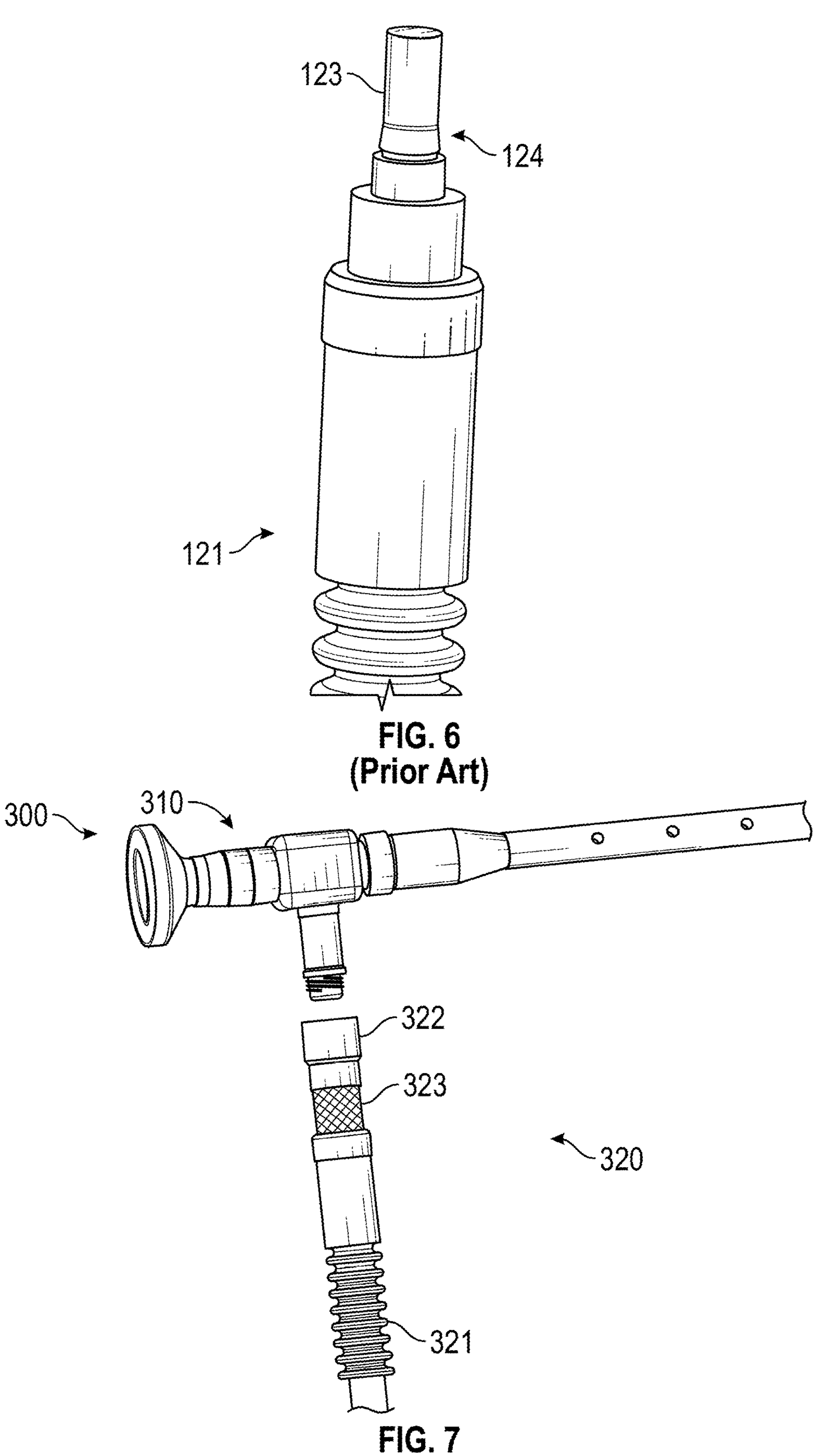
FIG. 6 shows the distal end of a conventional fiberoptic cable with the conventional connector removed.
FIG. 7 shows a laparoscopic instrument and a fiberoptic cable disconnected from the instrument, wherein an exemplary safety adaptor is mounted over the connector at the end of the fiberoptic cable.

FIG. 6 shows a detailed view of the distal end of the cable 121 with the connector 122 removed. The cable 121 can include a groove 124 below the distal tip 123 that is used to hold a snap ring, and thus the connector 122 or 222, in place. Internal threads can be included in the connector 122 and 222 and used to attach the connector to the optical instrument and in so doing pull the tip 123 of the fiberoptic cable into contact with a mating tip in the instrument. As shown in FIG. 5, the connector 222 has an elongated upper sheath 224 that enables the tip 223 to be hidden (FIG. 4) from exposure when not attached to the instrument.

The distal end of the sheath 224 of the connector 222 can be open to allow free passage of an externally threaded portion of the instrument into the connector to mate with an internally threaded region inside the connector. Alternative connections other than threaded connections can also be included. The open distal end 226 of the connector 222 allows light from the tip 223 of the optical fiber to escape longitudinally, but also allows the light to spread out to some extent after the light travels the axial distance from the tip 223 to the distal end 226 of the connector, thereby reducing the intensity of the light per unit of cross-sectional area as it leaves the connector 222. The open distal end 226 also allows ventilation of the inner region of the connector 222, and reduces heat buildup inside the connector that can occur when a cap is covering the distal end of the connector.

The diameter of the distal end of the connector 222 can be larger than the diameter of the proximal portion of the connector and/or can be larger than the diameter of the fiberoptic cable. This larger diameter can cause the distal end of the connector 222 to prop up the end of the cable when resting on a flat surface, such that the axis of the light emitted from the cable is tilted slightly upwardly from horizontal. This can reduce the likelihood of the light being directed at and/or damaging a surface (e.g., a surgical drape) on which the cable is resting.

Figures 8A, 8B, 9:
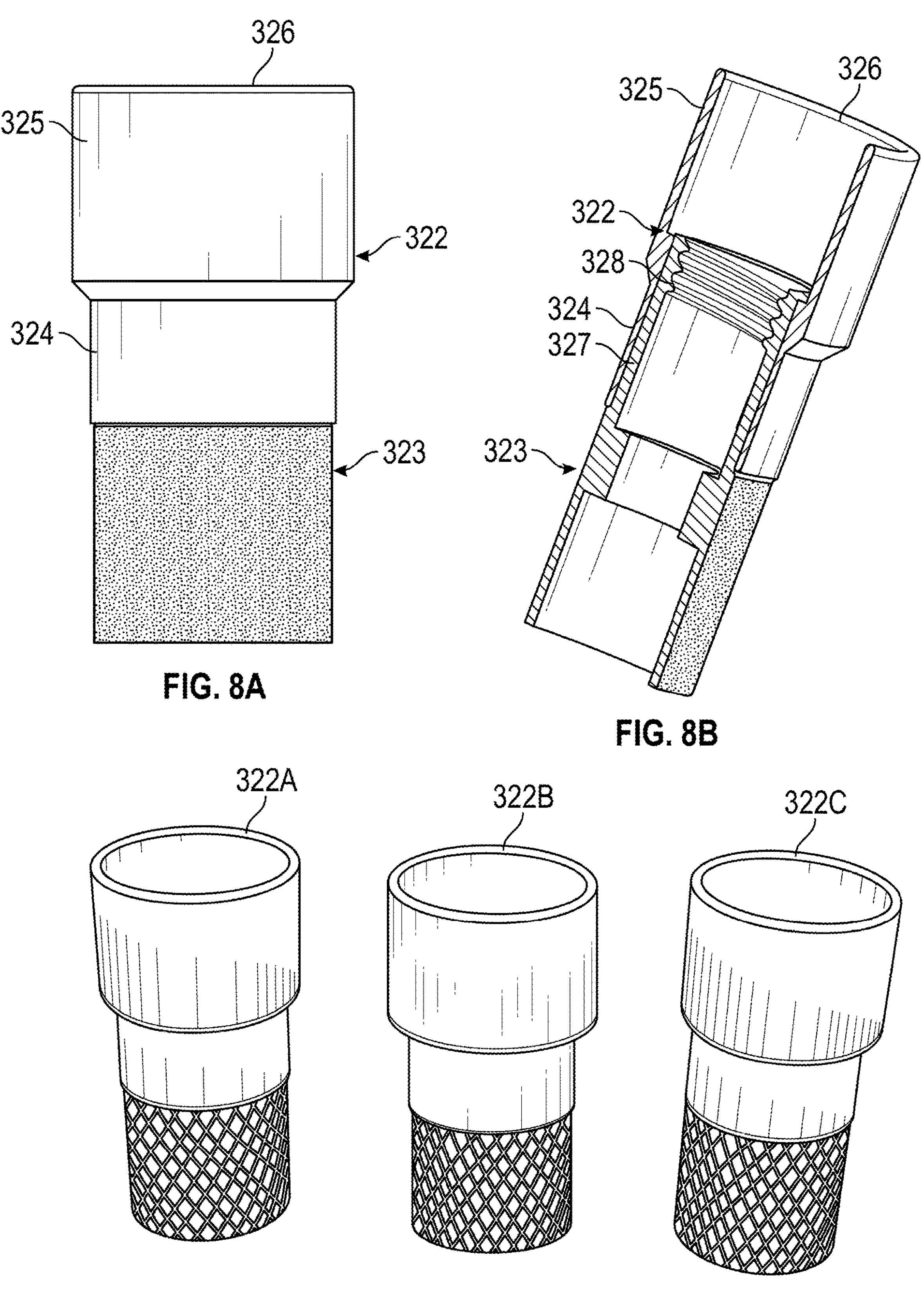
FIG. 8A shows the exemplary safety adaptor of FIG. 7 coupled to a conventional connector that is conventionally included at the end of the cable.
FIG. 8B is a cross-sectional perspective view of safety adaptor and conventional connector of FIG. 8A, showing the adaptor mounted around the outer surface of the connector and extending distally beyond the end of the connector.
FIG. 9 shows three exemplary embodiments of the safety adaptor shown in FIGS. 8A and 8B, each made from a different material. From left to right: PEEK, stainless steel, and DELRIN® (polyoxymethylene).

FIGS. 7-9 show an assembly 300 that includes an optical instrument 310 and a fiberoptic cable assembly 320 comprising a cable 321, a connector 323 (which can also be referred to as a "fiberoptic cable connector"), and an exemplary safety adaptor 322 that is mounted on the end of the connector 323. The connector 323 can be a conventional connector similar to the connector 122. Rather than requiring removal of the original connector, in this embodiment the adaptor 322 attaches to the original connector 323, such as by way of a press fit (for permanent attachment) or transitional fit (if removal by the user is desired). A practitioner, technician, retrofitter, or manufacturer can simply attach the adaptor 322 to the fiberoptic cable connector 323 by pressing it over the end or otherwise mounting it onto the end of the connector. The adaptor 322 serves as a shroud to extend the connector 323 distally and protect against contact with the optical fiber tip, while permitting the connection and disconnection between the connector and the instrument in the typical manner.

FIG. 7 shows a schematic of an exploded view of the instrument 310 and fiberoptic cable assembly 320 that has the adaptor 322 press fit onto the original cable connector 323. In this system, the tip of the fiberoptic cable is not exposed (compare to FIG. 2). FIG. 8A shows the adaptor 322 attached to the original connector 323, and FIG. 8B shows a section view of the adaptor and connector showing how they are connected. The adaptor includes a base 324 that is mounted around a distal end 327 of the connector 323, and a distal sheath 325 that extends distally a distance from the distal end of the connector and terminates in a distal opening 326. The opening 326 allows an externally threaded connector of the optical instrument 310 to be inserted through the sheath 325 and mate with internal threads 328 of the connector 323.

When tested, the adaptor 322 ensures that the fiberoptic tip cannot come into contact with a surface causing it to overheat or burn. Two sets of tests were carried out using the adaptor 322 involving direct and indirect light exposure from the tip of the cable, as arranged in the assembly 320 shown in FIG. 7. While the adaptor 322 was tested in the arrangement of FIG. 7, the safety connector 222 in the arrangement of FIG. 4 is functionally equivalent and can be expected to produce similar results as the adaptor 322 in combination with the existing connector 323.

In a hospital setting, after an optical instrument is disconnected, fiberoptic cables are often left lying flat on their side on the hospital drape, patient garment, the patient's skin, a table, or other surfaces, causing indirect/partial exposure to light and/or heat emitted from the cable. Accordingly, testing was conducted to measure the disclosed safety adaptors' effectiveness in such a situation. To test this use case, three embodiments of the adaptors 322 made of different materials were tested by laying the cable assembly 320 (comprising the fiberoptic cable 321, the connector 323, and the adaptor 322) flat on its side on a surgical drape (see FIG. 10) for five minutes. Measurements of the adaptor 322 and drape temperatures were recorded every twenty seconds. A control test was carried out to measure temperatures without the adaptor.

Figure 10:
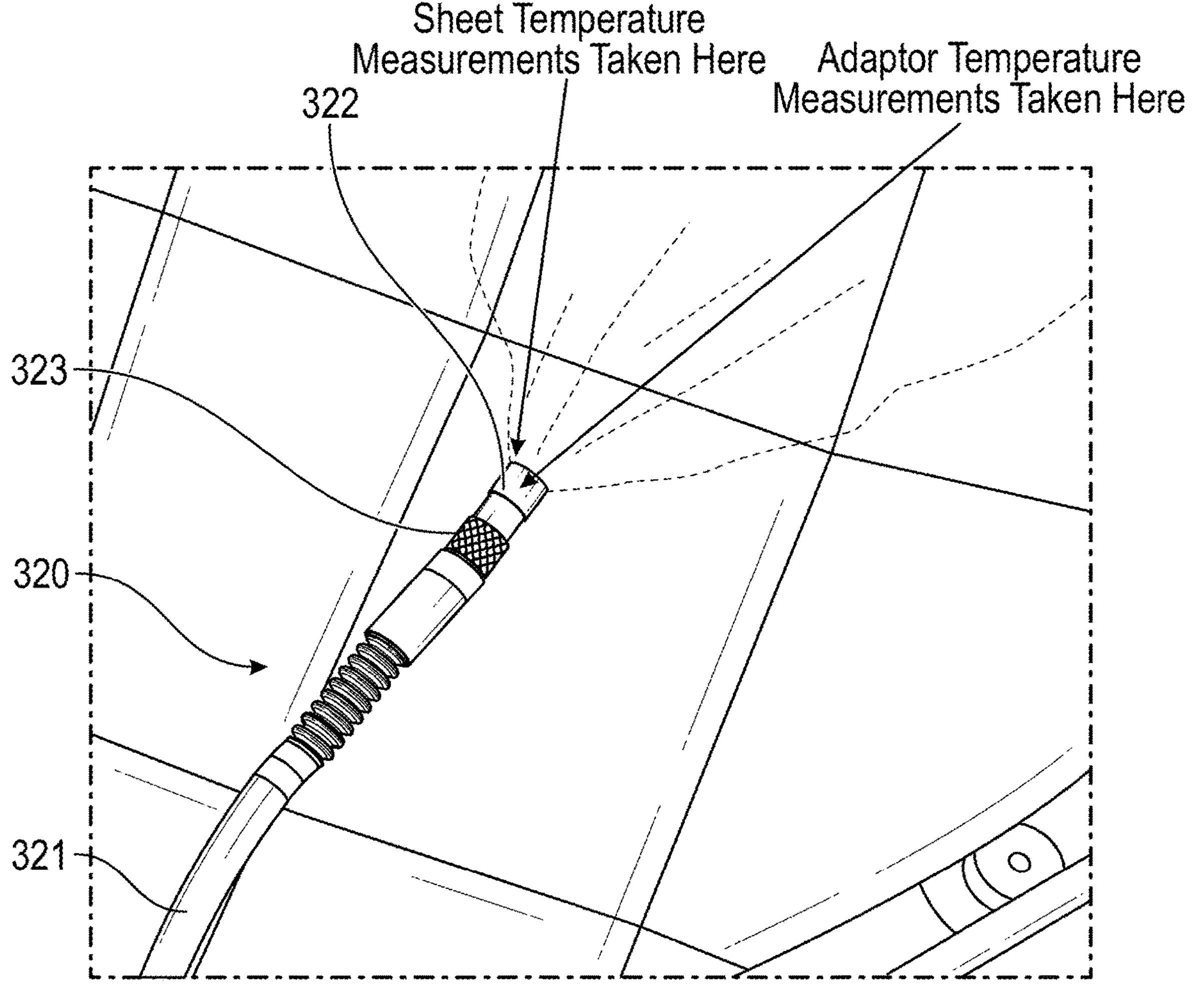
FIG. 10 shows a test setup with an active fiberoptic cable with a safety adaptor lying flat on surgical drape, and illustrates measurement locations for sheet and adaptor temperatures.

FIG. 9 shows the three tested adaptors 322 pressed onto original connectors (the fiberoptic cable is not shown). The test adaptors 322 were made using three different materials: PEEK (322A), stainless steel (322B), and Delrin (322C). FIG. 10 shows the test setup for indirect exposure in which the three different adaptor materials were tested, along with the control case (original cable 321 and connector 323 with no safety adaptor). In the tests, the fiberoptic cable was turned on (conducting light) and placed on a hospital drape allowing it to indirectly shine light on the drape for five minutes. Temperatures were recorded every 20 seconds. Results are shown in FIGS. 11-14.

Figure 11:
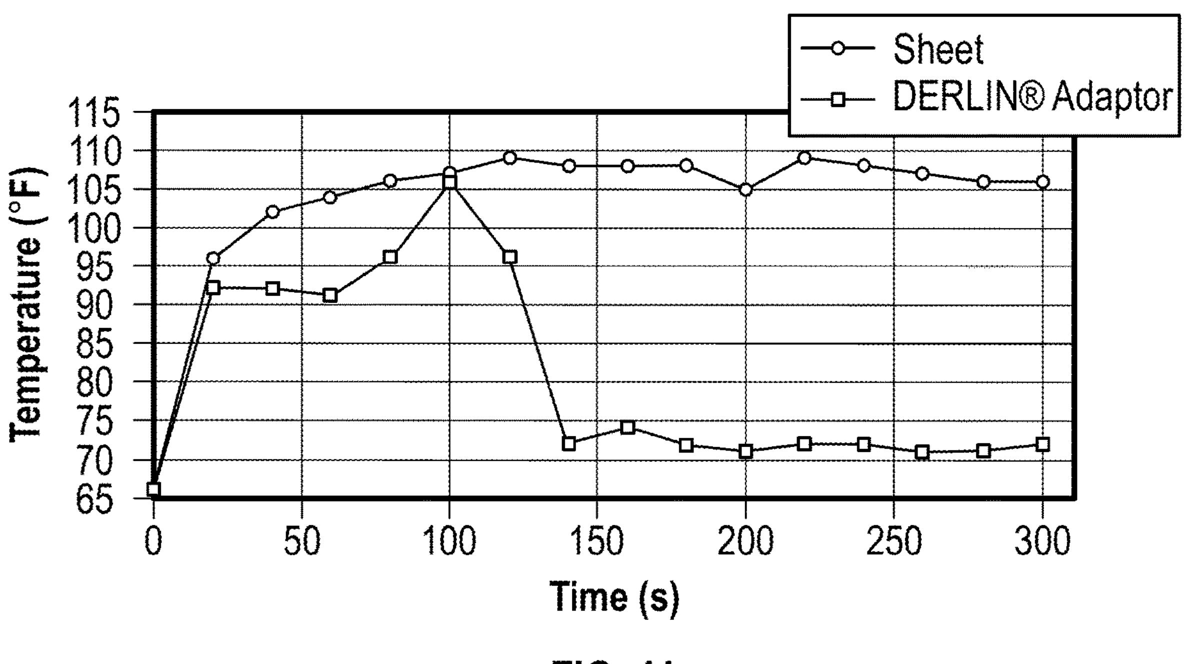
FIG. 11 is a graph showing the changes in the temperature at the adaptor surface and at the surgical drape over time when the DELRIN® safety adaptor is used.
Figure 12:
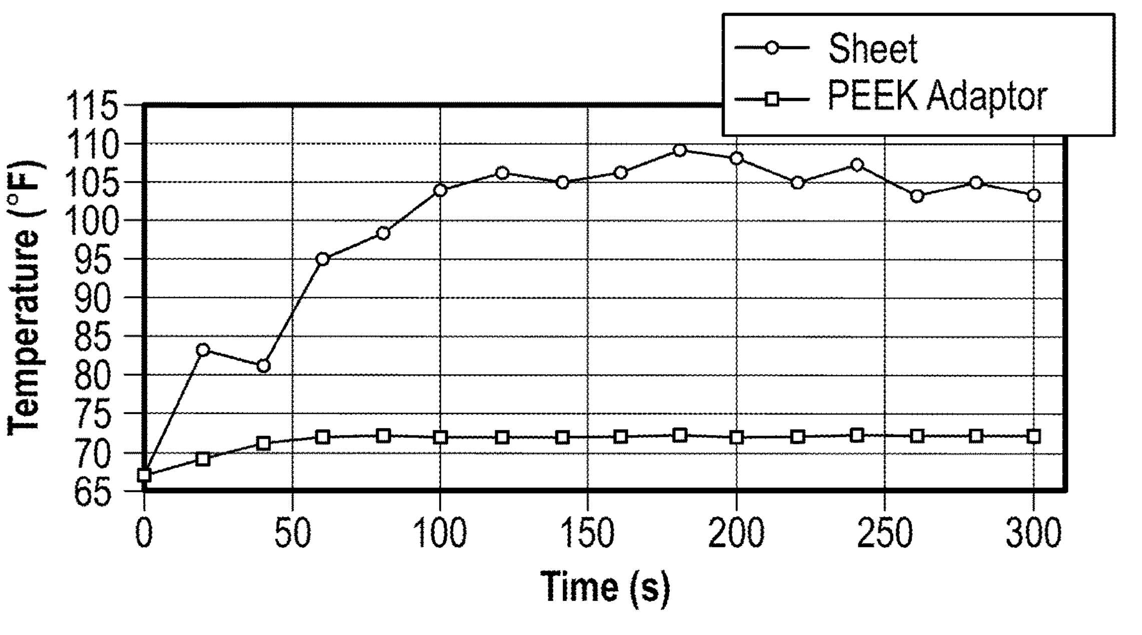
FIG. 12 is a graph showing the changes in the temperature at the adaptor surface and at the surgical drape over time when the PEEK safety adaptor is used.
Figure 13:
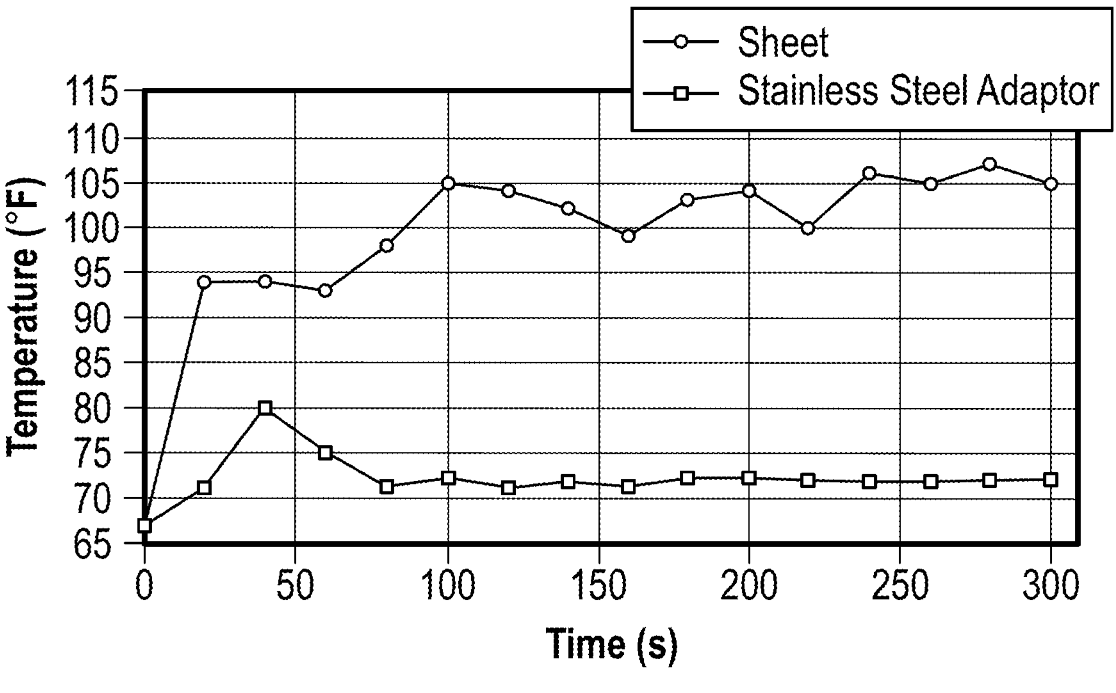
FIG. 13 is a graph showing the changes in the temperature at the adaptor surface and at the surgical drape over time when the stainless steel safety adaptor is used.
Figure 14:
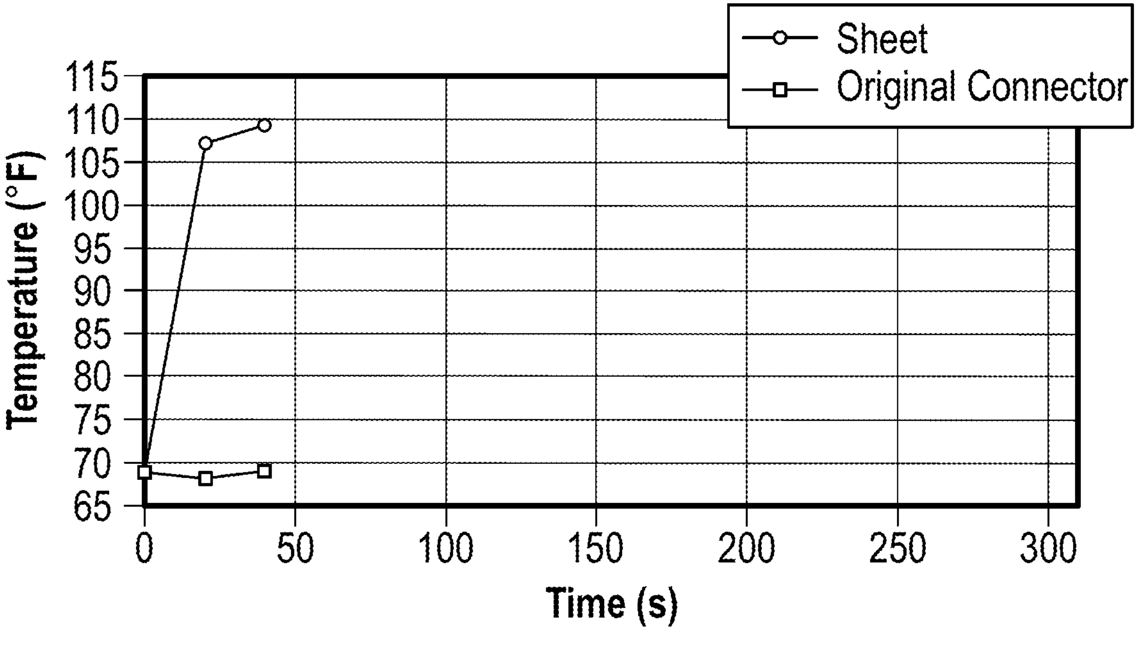
FIG. 14 is a graph showing the changes in the temperature at the connector surface and at the surgical drape over time when no safety adaptor is attached to the cable.

In FIG. 11, the graph shows that the temperature of the Delrin adaptor peaked around 105° F. in 100 seconds but then leveled off around 72° F. The temperature of the sheet increased and remained around 105° F. FIG. 12 shows that for the PEEK adaptor, the temperature of the adaptor remained at a constant 72° F. for the duration of the test. The temperature of the sheet increased to maximum of 110° F. In FIG. 13 the results for the stainless steel adaptor show that the temperature of the adaptor peaked at 80° F. then remained around 72° F. for the duration of the test. The temperature of the sheet increased then remained between 105° F. and 107° F. Finally, the control test results are shown in FIG. 14, in which the connector temperature (which in this case is the original connector) remained fairly constant around 70° F. The temperature of the sheet peaked at 109° F. then burned a hole through the drape within 50 seconds.

Figure 15:
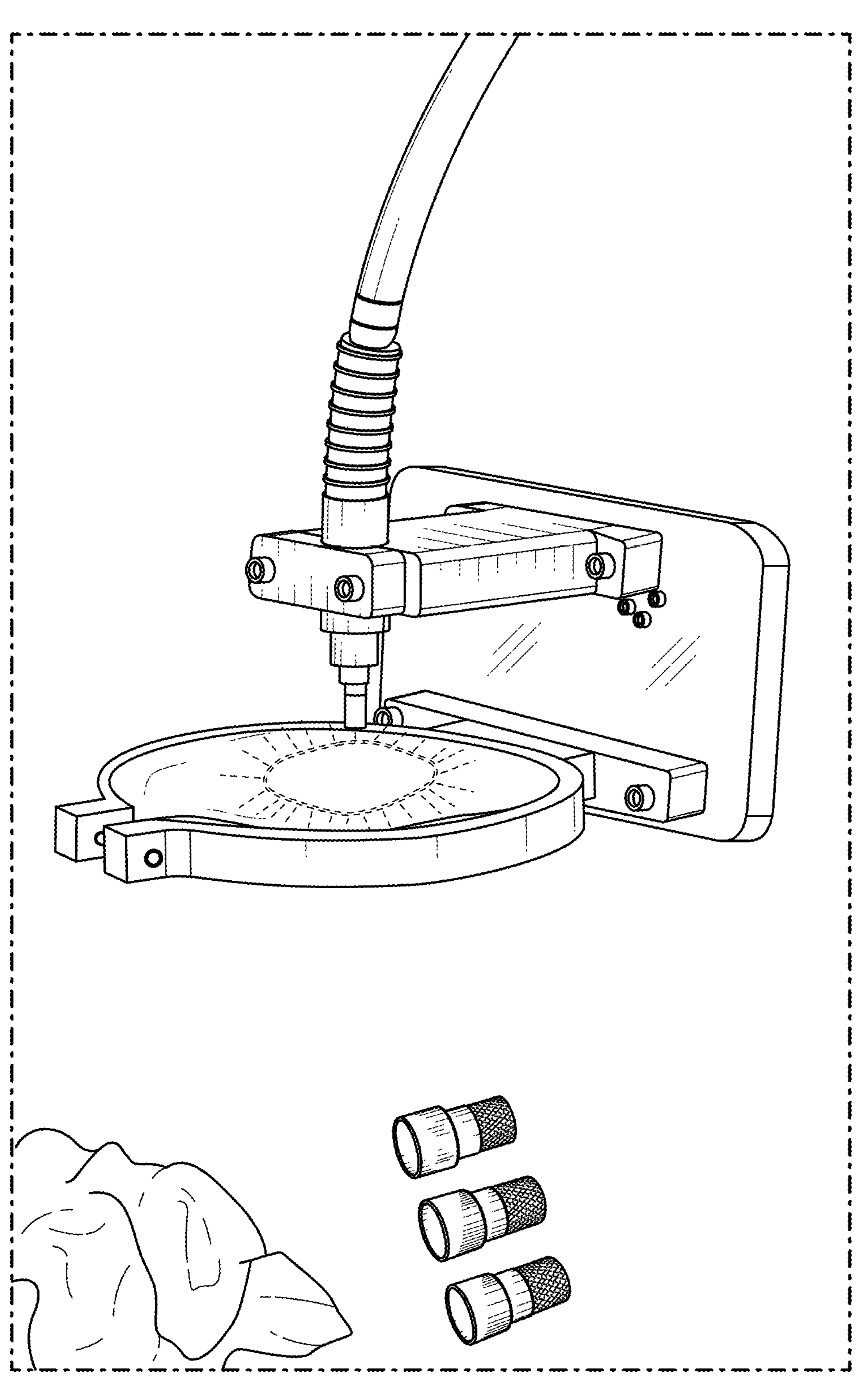
FIG. 15 shows a test setup where light from the end of a fiberoptic cable is directed at a perpendicular piece of surgical drape.

FIG. 15 shows a photograph of a direct light exposure test. In this test the fiberoptic cable was held such that its emitted light shined directly on a piece of hospital drape at various distances up to 12 mm. At any distance within this range, in each of the tests (for PEEK, stainless steel, Delrin, or no adaptor) the direct light burned a hole through the hospital drape within 45 to 50 seconds. It was concluded that while sufficient to protect surgical drapes and skin from burns due to indirect exposure to emitted light from the fiberoptic cable as in FIG. 10, an alternative safety adaptor design is needed to protect against direct exposure as in FIG. 15.

To provide the properties of protection from indirect exposure of light and heat from the end of the fiberoptic cable, as provided by the embodiments of FIGS. 1-9, and to also prevent overheating, fires, or burns from direct exposure of the light, some embodiments can include a protective end cover to blocks and/or diffuses the light emitted axially from the end of the cable.

Some embodiments include a spring-loaded sheath (not shown) that increases the distance between the end of the light cable and an exposed surface by a greater distance than a fixed sheath as described above. For example, in some embodiments the safety device can include a fixed base portion that mounts to the connector and an axially articulating distal sheath portion that is coupled to the base portion via at least one spring or other biasing mechanism. When the optical instrument is not attached, the spring can urge the sheath portion to a distal, extended position where the distance from the end of the optical fiber to the end of the sheath portion is a maximum distance. When proximal force is applied to the sheath portion, such as when an optical instrument is inserted into the device for connector to the cable, the spring can be compressed allowing the sheath portion to move proximally toward the base portion sufficiently to allow connection of the optical instrument. When the optical instrument is disconnected and removed from the connector, the compressed spring automatically pushes the sheath portion back distally to its maximally extended position to provide increased protection from damage from the light emitted from the cable. In some embodiments, the base portion and the sheath portion can maintain at least some overlap even in the maximally extended position to prevent light from escaping radially. In some embodiments, a flexible material is positioned between the base portion and the sheath portion to block light from escaping radially. In some embodiments, the sheath portion and the base portion have a telescoping engagement wherein one overlaps and slides over the other.

Figure 16A:
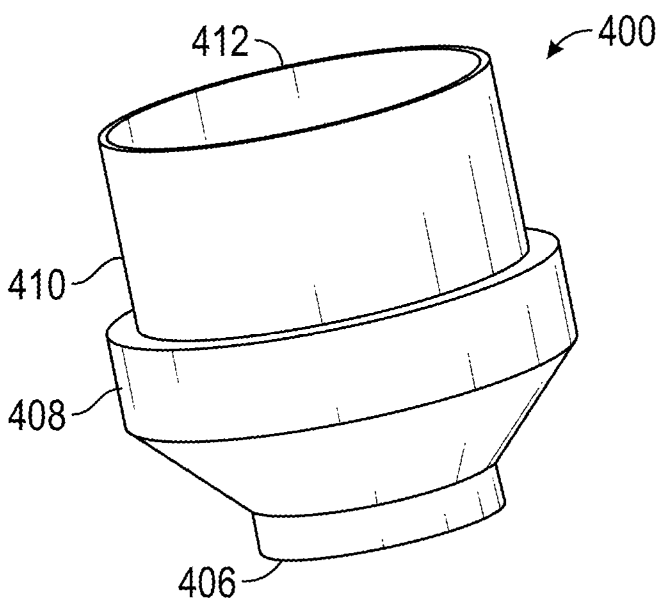
FIG. 16A shows another exemplary safety adaptor configured to be coupled to an existing connector at the end of a fiberoptic cable.
Figure 16B:
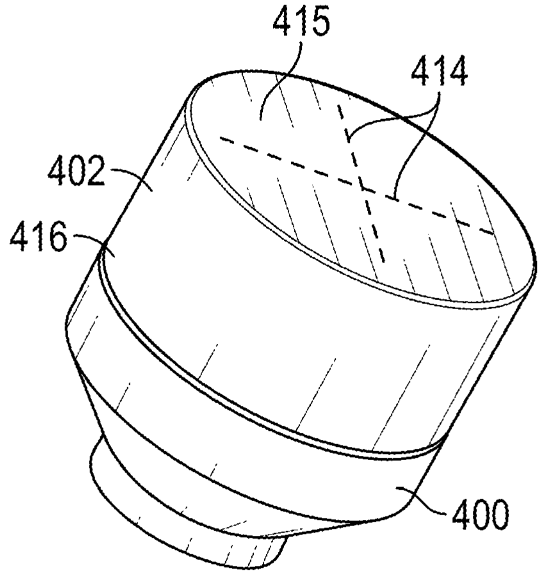
FIG. 16B shows the adaptor of FIG. 16A with a slit cover positioned over the open end of the adaptor.

FIGS. 16A-E illustrate an exemplary assembly that includes a modified adaptor 400 that mounts onto a connector 404 at the end of a fiberoptic cable and an end cover 402 that is positioned over the distal opening 412 of the adaptor 400. Note that the connector 404 can be the same as the connectors 122 and 323, or a different connector. Alternatively, the connector 404 can be part of the assembly with adaptor 400 that is made to replace an existing connector at the end of a fiberoptic cable. FIG. 16A shows the modified adaptor 400, which is configured to accommodate the light blocking/diffusing end cover 402 (compare the change in shape to that shown in FIG. 5 and FIG. 9). The adaptor 400 includes a proximal opening 406 sized to engage the connector 404, a broad shoulder 408, and a distal shelf portion 410 of reduced outer diameter relative to the shoulder 408, such that a circumferential rim 416 of the end cover is seated over the shelf portion 410 (see FIG. 16E). FIG. 16B shows the adaptor 400 with the end cover 402 attached, and FIG. 16C shows the end cover 402 isolated. The end cover 402 may be a permanent, semi-permanent, or removable and replaceable component separate from the adaptor 400, as illustrated, or the cover and adaptor may be integrated as single piece. In some embodiments, the entire assembly can be made of one material, or multiple materials combined together. FIG. 16D shows the full assembly of the adaptor 400 and cover 402 attached to the original connector 404, and FIG. 16E shows a sectional view of the assembly of FIG. 16D. Internal threads 418 in the original connector 404 for connecting to the fiberoptic instrument are shown in FIG. 16D.

Figure 17:
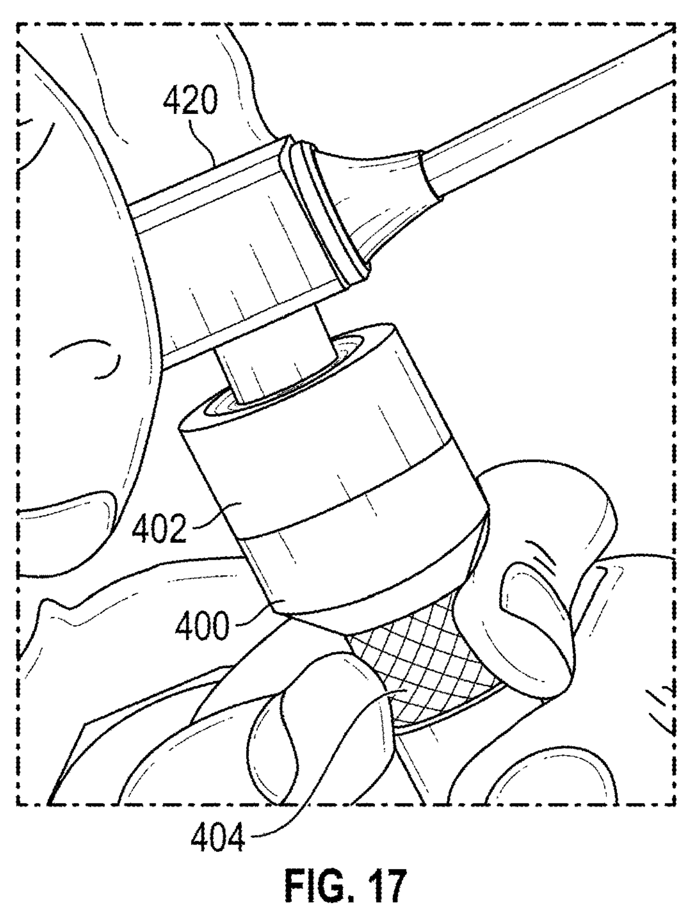
FIG. 17 shows an exemplary embodiment of a fiberoptic cable with the adaptor and cover of FIG. 16B mounted on the connector at the end of the cable, and with a laparoscopic instrument extending through the slit in the cover and connecting to the connector.
Figure 18:
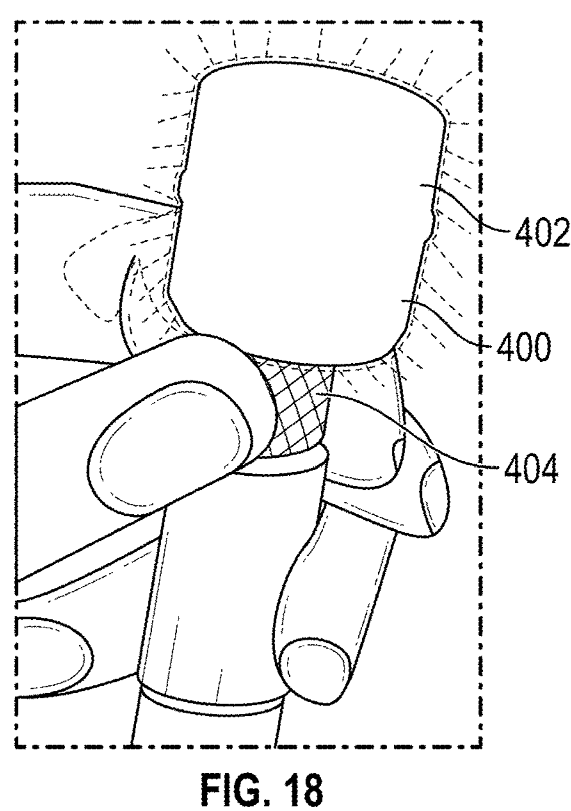
FIG. 18 shows the cable, adaptor and cover of FIG. 17 with the laparoscopic instrument removed and light from the end of the cable being blocked and dissipated through the adaptor and cover.

The end cover 402 comprises one or more slits or slots 414 in the distal cover portion illustrated as a dashed "+" shape or cross shape, although many slit shapes may alternatively be used, such as a star shape, asterisk shape, or other shape having intersecting slits). The slits 414 enable the fiberoptic instrument to be inserted into the connector 404 by passing through the cover 402, as shown in FIG. 17. The male connector of the instrument is forced down through the slits 414 in the cover and the slits create flaps 415 that elastically deform radially outwardly and downwardly into the adaptor 400 when the instrument is inserted. In this way, a user can insert the male connector of the instrument into the female threaded portion 418 of the connector 404, attaching it to the fiberoptic cable, without doing anything differently than when the same process is performed with a fiberoptic cable that does not include the adaptor 400 or cover 402. Thus, the user's conventional routine does not need to be modified when the adaptor 400 and cover 402 are mounted to the connector 404. When the instrument is to be removed, the connector 404 can be unscrewed (or otherwise disconnected as it normally would be) and the instrument can be simply lifted out through the cover 402. The flaps 415 in the cover 402 resiliently return back to their original positions shown in FIG. 16C with the slits 414 closed (or nearly closed), effectively blocking the light emitted from the tip of the cable from exiting axially from the adaptor 400, as shown in FIG. 18. In some embodiments, the slits 414 can be formed at an angle from the longitudinal axis so that there is not a direct path for light to travel from the tip of the optical fiber through the slit and out of the end cover. Rather, when the slits are formed at an angle from the longitudinal axis, the two sides of the slit can overlap longitudinally to block light from escaping in the longitudinal direction.

Materials for the adaptor 400 and cover 402 can be selected from any materials that block a sufficiently amount of the light and maintain a sufficiently low temperature when positioned over the end of an energized fiberoptic cable for an extended time to reduce or eliminate the risk of burns to patients, surgical drapes, and other objects. For example, in the embodiment illustrated in FIGS. 17 and 18, the cover 402 is made of a 30 durometer silicone with white pigment. The adaptor 400 can be made of PEEK (as shown in FIG. 17) or acrylic (as shown in FIG. 18), for example.

As shown in FIG. 18 for example, some light can diffuse through the adaptor and cover assembly, which can cause the assembly to glow. By emitting some of the light, heat can be steadily dissipated to prevent the assembly from getting too hot, and allowing the assembly to reach a safe steady-state temperature over time. The opacity/transmissivity of the adaptor 400 and the cover 402 can depend on the particular materials and thicknesses of the adaptor and the cover, and accordingly the materials and thicknesses of the adaptor and the cover can affect the amount of light emitted from the assembly and its steady-state temperature. The more opaque the material, the greater the steady-state temperature, as more opacity allows less of the light to escape and traps more heat energy within the assembly.

Figure 19A:
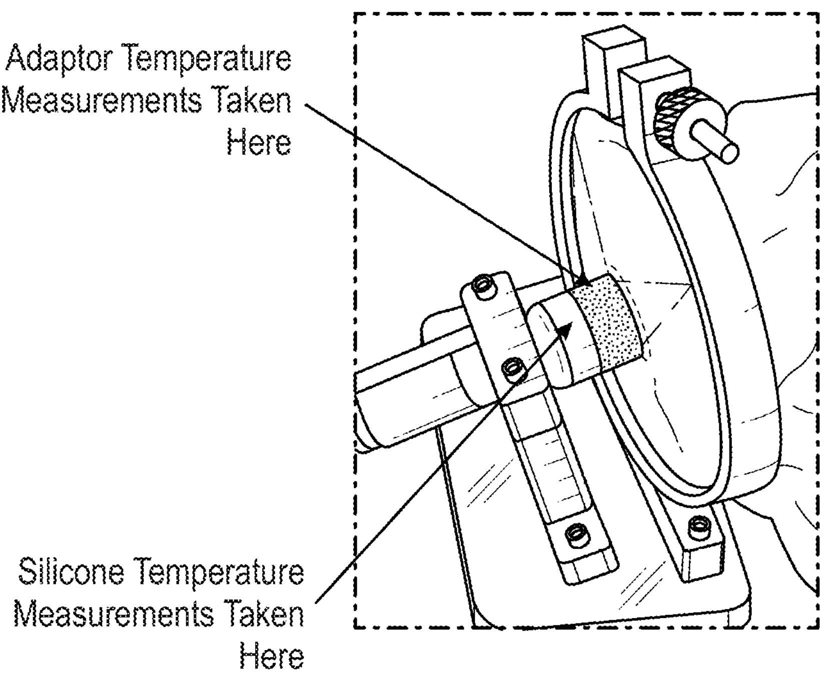
FIG. 19A shows a test setup wherein an active fiberoptic cable with the adaptor and cover as shown in FIG. 18 is positioned with the cover flat against a piece of surgical drape.
Figure 19B:
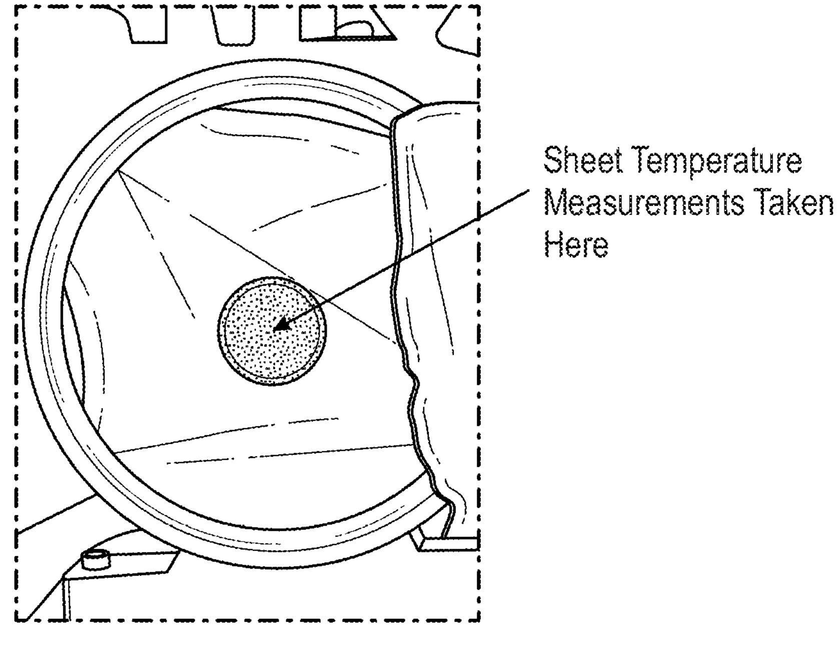
FIG. 19B shows a back side of the piece of surgical drape, where temperature measurements were taken.

To test the effectiveness of the adaptor 400 and end cover 402 mounted on the connector 404 (as shown in FIGS. 16 and 18), the fiberoptic cable assembly was held so that its end was perpendicular to a hospital drape with the cover just touching the drape (as shown in FIG. 19). The light was on for three minutes. In the testing, the adaptor 400 was made of either PEEK or acrylic, and the end cover 402 was made of silicone. Temperatures of the end cover 402, adaptor 400, and drape were measured with a non-contact infrared temperature sensor every minute until the conclusion of the three minute interval. The tests were repeated for a total of three trials for each of the PEEK and acrylic adaptors.

Figure 20:
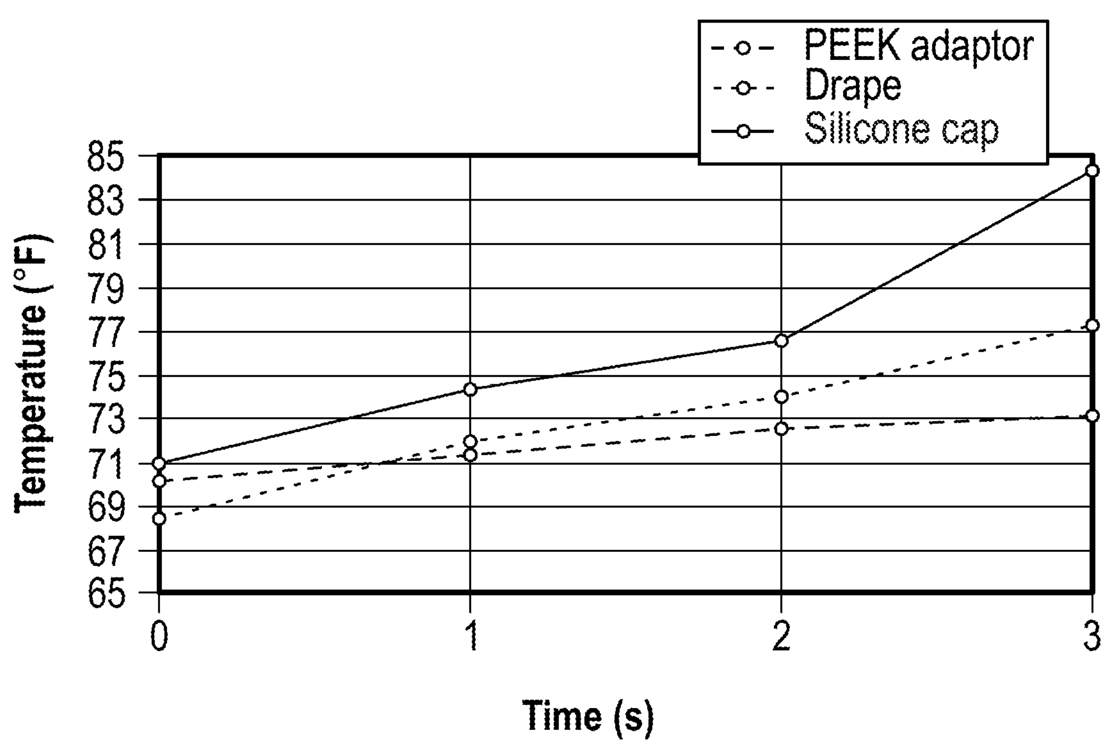
FIG. 20 is a graph showing changes over time in the temperature of the adaptor, the cover, and the drape, when a PEEK adaptor was used.
Figure 21:
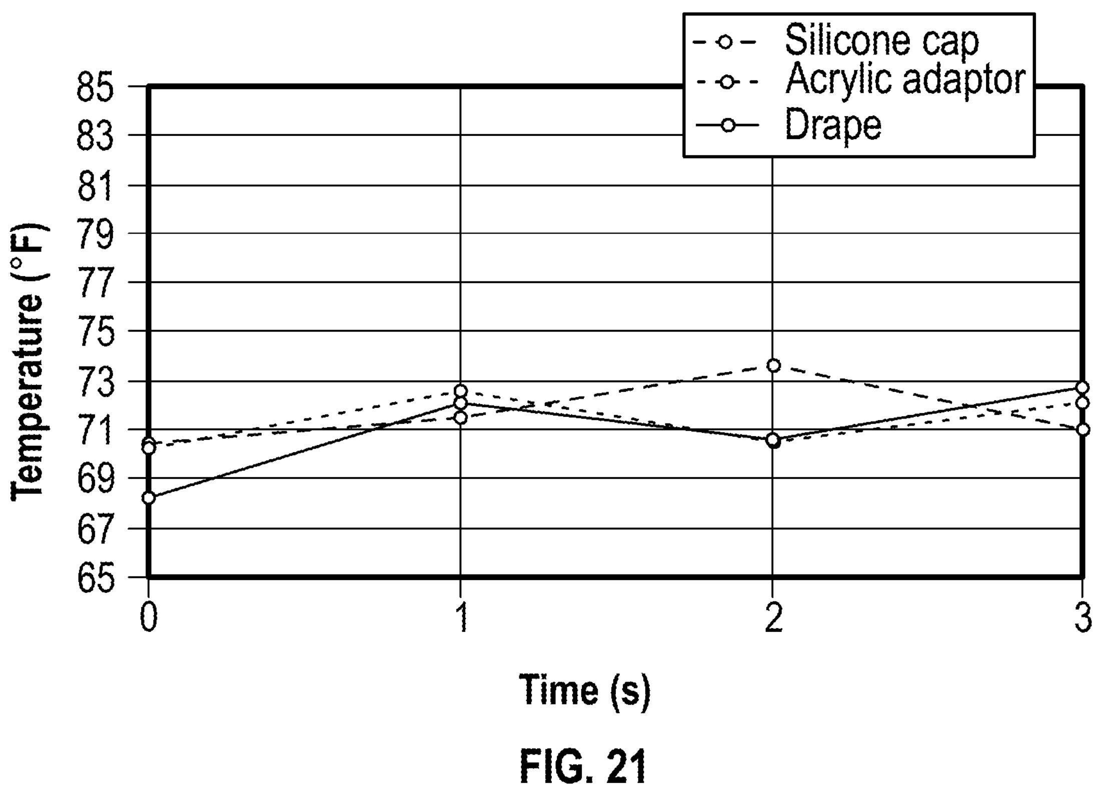
FIG. 21 is a graph showing changes over time in the temperature of the adaptor, the cover, and the drape, when an acrylic adaptor was used.

FIGS. 20 and 21 show the average measured temperatures of the adaptor, cover, and drape during testing at one minute intervals. FIG. 20 shows results with a PEEK adaptor, and FIG. 21 shows results with an acrylic adaptor. The graph of FIG. 20 shows that when the PEEK adaptor was used, the temperatures remained between 68° F. and 85° F. for the duration of the test, and FIG. 21 shows that with the acrylic adaptor the temperatures remained between 68° F. and 74° F. While the temperatures for the PEEK adaptor specimens had not reached steady-state, it is evident from the graph that they had for the acrylic adaptor.

Because the temperatures of the PEEK adaptor specimens had not reached steady state, the tests were repeated for one specimen of each type (PEEK and acrylic) for a duration of ten minutes. At the end of the ten minute test, the temperatures of the adaptor, silicone cover, and drape were 83° F., 100° F., and 82° F., respectively, for the PEEK adaptor specimen, and 79° F., 77° F., and 78° F. for the acrylic adaptor specimen.

Both specimens maintained the drape at a very safe temperature during the testing, although the silicone cover became very hot to touch when the PEEK adaptor was used. It is believed that the reason for the difference in performance is that the more transparent acrylic material allowed more energy to escape from the adaptor that was otherwise trapped and converted to heat in the PEEK adaptor. Even though the PEEK adaptor was hotter than the acrylic adaptor, it provided a much delayed transfer of heat to surrounding objects than when no adaptor was used.

Figure 22:
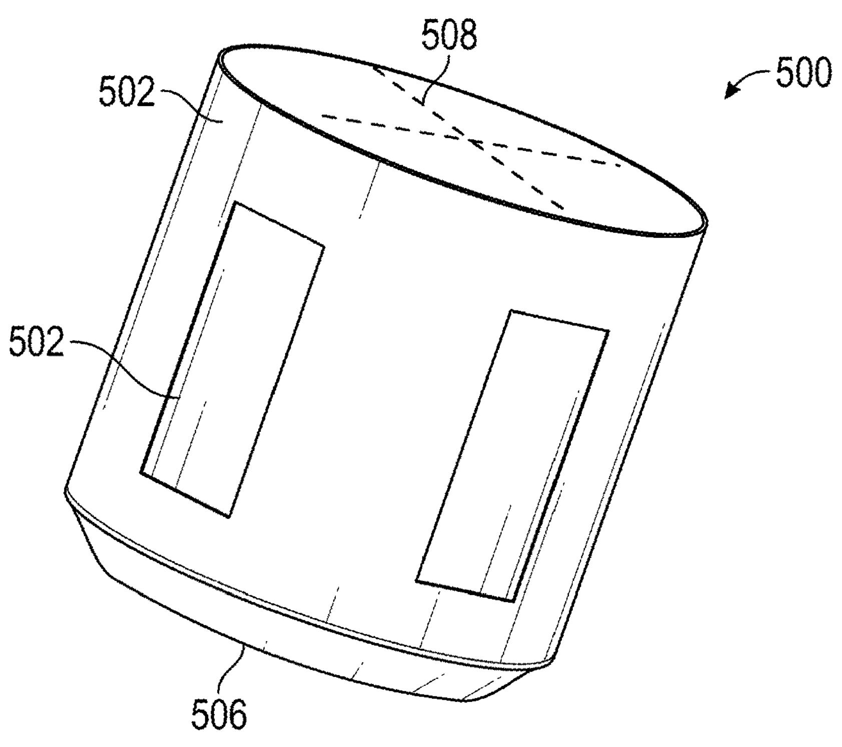
FIG. 22 shows an exemplary safety device comprising a semi-rigid skeleton adaptor and a flexible overmold covering that include a slit end cover and window portions.
Figure 23:
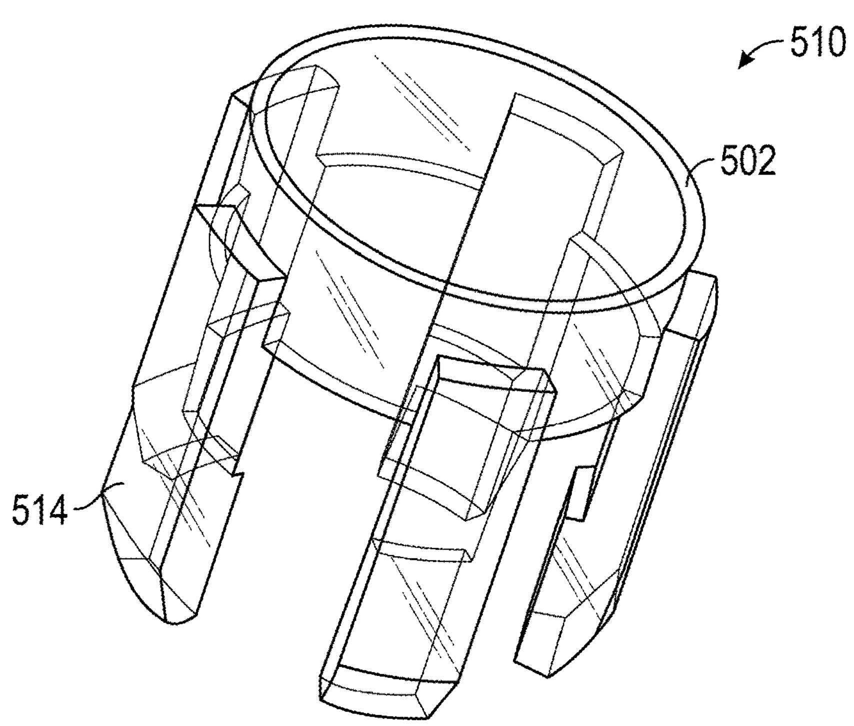
FIG. 23 shows the skeleton adaptor of the device of FIG. 22.

In some embodiments, safety adaptors can include one or more transparent or partially transparent window regions and other fully or partially opaque portions between the windows regions. In some embodiments, the adaptor can comprise a skeleton-like structure and/or comprise a plurality of fingers that are covered with an elastic, transparent or opaque material, such as a silicone overmold material. Such embodiments can be more flexible and adaptable to be mounted over various sized connectors that have different diameters, while also allowing some light to escape. For example, FIGS. 22 and 23 show an exemplary safety adaptor 500 that includes a semi-rigid skeleton 510 covered with a flexible overmold 502. The overmold 502 can comprise silicone and/or other elastic material. The safety adaptor 500 can optionally also comprise one or more windows 504 in the overmold 502 or other transparent portions that allow some of the light to escape from within. The windows 504 can comprise different material from the rest of the overmold 502 and/or can be otherwise more transparent. The safety adaptor 500 can include an open proximal end 506 that is mountable over different sized connectors at the end of a fiberoptic cable. The skeleton 510 can include a distal ring portion 502 and a plurality of fingers 514 projecting proximally from the ring portion 502. The fingers 514 can flex radially relative to the ring 502 to allow the diameter of the proximal opening 506 to fit over various sized connectors. The overmold 502 also flexes along with the fingers 514 and can serve as a spring material to provide constraining force on fingers 514 to enhance the friction force that secures the adaptor to the connector. The skeleton 510 can comprise an at least partially transparent material such that the windows 504 are positioned to occupy the full or partial width of the fingers, or the windows 504 can be positioned between the fingers 514 as openings in the overmold. The distal end of the safety adaptor 500 can include slits 508 in the portion of the overmold 502 that spans across the top of the ring portion 502. The slits 508 can have the same properties and functionality as the slits 414 in the embodiment 400, blocking light from escaping axially out of the safety adapter when the optical instrument is removed and flexing inwardly out of the way when the optical instrument is inserted through the ring 502 and connected to the connector within the safety adaptor 500.

CONCLUSION

It has been shown that the connectors, adaptors, end covers, and associated assemblies disclosed herein successfully protect users, patients, surgical drapes, and other objects from burns, fires, and overheating due to direct contact with the tip of the optical fiber tip, thermal heat conduction through the components, indirect exposure to emitted light, and/or direct exposure to emitted light when the optical instrument is disconnected from the fiberoptic cable by providing physical spacing from the tip of the optical fiber, providing a circumferential sheath, and/or providing a light-occluding slit end cover, made of materials and dimensions of sufficient thermal conductivity and optical transmissivity, all while allowing optical instruments to be readily connected and disconnected from the cable without change in the methodology compared to conventional setups.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A safety device for a fiberoptic cable for use in medical procedures, the safety device comprising:

an annular adaptor; and an end cover coupled to the annular adaptor, wherein the end cover comprises a resiliently deformable material and includes a flap that is moveable between a relaxed state and an elastically deformed state, wherein the flap comprises an attachment edge and a free, unattached boundary portion, wherein a portion of a perimeter of the flap is attached to the annular adaptor along the attachment edge, wherein a remaining portion of the perimeter of the flap forms the free, unattached boundary portion, wherein the unattached boundary portion comprises a distal edge along a distal face of the flap, a proximal edge along a proximal face of the flap, and a thickness extending between the proximal edge and the distal edge;

wherein the annular adaptor comprises an elastomeric sleeve so dimensioned as to receive a connector disposed at a distal end of a fiberoptic cable such that the end cover of the safety device is distal of a distal end of the connector;

wherein, relative to the flap in the relaxed state, the flap is deformed radially outwardly from a longitudinal axis of the safety device in the elastically deformed state, and wherein, relative to the flap in the relaxed state, at least a portion of the free, unattached boundary portion of the flap is displaced along the longitudinal axis of the safety device in the elastically deformed state;

wherein the safety device is sized and shaped such that, when the connector of the fiberoptic cable is coupled to an engagement portion of an optical medical instrument, the flap is configured to be maintained in the elastically deformed state, and wherein the safety device is sized and shaped such that, when the connector of the fiberoptic cable is uncoupled from the engagement portion of the optical medical instrument, the flap is configured to move from the elastically deformed state to the relaxed state such that light emitted from the fiberoptic cable is at least partially blocked by the end cover.

2. The safety device of claim 1, wherein the end cover comprises a partially light transmissive material, the partially light transmissive material configured to transmit a portion of light incident on an inner surface of the end cover and thereby provide a visual indicator that the fiberoptic cable is conducting light.

3. The safety device of claim 1, wherein the resiliently deformable material is silicone.

4. The safety device of claim 1, wherein the end cover and the annular adaptor are integrally formed.

5. The safety device of claim 1, further comprising at least one flexible finger extending between the annular adaptor and the end cover.

6. The safety device of claim 1, wherein the annular adaptor comprises a proximal opening and a distal opening.

7. An assembly comprising:
the safety device of claim 1;
the fiberoptic cable with the connector; and
an optical medical instrument comprising an engagement portion;
wherein, when the distal connector of the fiberoptic cable is coupled to the engagement portion of the optical medical instrument, the fiberoptic cable is configured to transmit light to the optical medical instrument for use in a medical procedure.

8. The safety device of claim 1, wherein the end cover comprises a distal end wall and a circumferential side wall extending proximally from a perimeter of the distal end wall.

9. The safety device of claim 8, wherein, when the flap is in the relaxed state, a distal end of the safety device is a flat surface formed by an exterior side of the distal end wall.

10. The safety device of claim 1, wherein the elastomeric sleeve of the annular adapter includes an inner distal face that is substantially perpendicular to the longitudinal axis of the safety device, wherein, when the flap is in the relaxed state, the flap of the end cover is axially offset from the inner distal face along the longitudinal axis of the safety device.

11. The safety device of claim 10, wherein, when the flap is in the relaxed state, the distal face of the flap of the end cover is distal of the inner distal face of the elastomeric sleeve.

12. The safety device of claim 10, wherein the end cover comprises a flexible portion that extends between the inner distal face of the annular adapter and the attachment edge of the flap of the end cover for axially offsetting the flap from the inner distal face.

13. An assembly for use in medical procedures, the assembly comprising:
a fiber optic cable; and
a safety device comprising:
an annular adaptor; and
an end cover coupled to the annular adaptor, the end cover comprising a resiliently deformable material, wherein the end cover is moveable between a relaxed state and an elastically deformed state and comprises a free edge;
wherein the annular adaptor is configured to receive a connector disposed at a distal end of a fiberoptic cable such that the end cover of the safety device extends distally relative to a distal end of the connector;
wherein, in the relaxed state, a plane of a distal face of the end cover is perpendicular to a longitudinal axis of the safety device, and wherein, in the elastically deformed state, a free edge of the end cover is deformed radially outwardly relative to the longitudinal axis and is axially displaced along a longitudinal axis of the safety device; and
wherein the safety device is sized and shaped such that, when the connector of the fiberoptic cable is coupled to an engagement portion of an optical medical instrument, the engagement portion of the optical medical instrument extends past the end cover and maintains the end cover in the elastically deformed state, and when the connector of the fiberoptic cable is uncoupled from the engagement portion of the optical medical instrument, the end cover moves from the elastically deformed state to the relaxed state such that light emitted from the fiberoptic cable is at least partially blocked by the end cover.

14. The assembly of claim 13, wherein the annular adaptor comprises an elastomeric sleeve configured to be friction fit around the connector of the fiberoptic cable.

15. The assembly of claim 13, wherein the end cover comprises a partially light transmissive material, the partially light transmissive material configured to transmit a portion of light incident on an inner surface of the end cover and thereby provide a visual indicator when the fiberoptic cable is conducting light.

16. A method of using a safety device for a fiberoptic cable, the method comprising:
inserting a connector at a distal end of the fiberoptic cable into an annular adaptor of the safety device such that an end cover of the safety device extends distally relative to the distal end of the connector, wherein the safety device comprises:
the annular adaptor; and
the end cover coupled to the annular adaptor, wherein the end cover comprises a resiliently deformable material and includes a flap that is moveable between a relaxed state and an elastically deformed state, wherein the flap comprises a free edge;
wherein the annular adaptor comprises an elastomeric sleeve so dimensioned as to receive the connector disposed at the distal end of the fiberoptic cable;
wherein, relative to the flap in the relaxed state, the flap is deformed radially outwardly from a longitudinal axis of the safety device in the elastically deformed state, and wherein, relative to the flap in the relaxed state, at least a portion of the free edge of the flap is displaced along the longitudinal axis of the safety device in the elastically deformed state;
deforming the safety device such that the flap transitions from the relaxed state to the elastically deformed state;
engaging the connector of the fiberoptic cable with an engagement portion of an optical medical instrument to couple the fiberoptic cable to the optical medical instrument and transmit light thereto, the coupling between the connector and the engagement portion maintaining the flap in the elastically deformed state; and
disengaging the connector of the fiberoptic cable from the engagement portion of the optical medical instrument, the disengaging of the connector and the engagement portion resulting in the flap resiliently transitioning from the elastically deformed state to the relaxed state such that at least a portion of the light emitted from the distal end of the fiberoptic cable is blocked by the end cover.

17. The method of claim 16, wherein the deforming the safety device such that the flap transitions from the relaxed state to the elastically deformed state results in displacement of at least a portion of the free edge of the flap along the longitudinal axis of the safety device.

18. The method of claim 16, wherein the end cover comprises a partially light transmissive material, and the method further comprises utilizing the end cover as a visual indicator to determine whether the fiberoptic cable is conducting light.

19. The method of claim 16, further comprising, after the uncoupling of the connector of the fiberoptic cable from the engagement portion of the optical medical instrument, placing the fiberoptic cable onto a surface, wherein the surface is protected from the light emitted from the distal end of the fiberoptic cable via the end cover including the flap in the relaxed state.

20. The method of claim 16, further comprising, after the uncoupling of the connector of the fiberoptic cable from the engagement portion of the optical medical instrument, placing the fiberoptic cable onto a surface, wherein the distal end of the fiberoptic cable is offset from the surface via the safety device.

* * * * *